(12) United States Patent
Raichman et al.

(10) Patent No.: US 9,773,402 B2
(45) Date of Patent: Sep. 26, 2017

(54) INFECTIOUS DISEASE SPREAD PREVENTION

(71) Applicant: HYGINEX ISRAEL LTD., Herzliya (IL)

(72) Inventors: Efrat Raichman, Herzliya (IL); Yossef Raichman, Herzliya (IL)

(73) Assignee: HYGINEX ISRAEL LTD., Herzliya (IL)

( * ) Notice: Subject to any disclaimer, the term of this patent is extended or adjusted under 35 U.S.C. 154(b) by 0 days.

(21) Appl. No.: 14/425,353

(22) PCT Filed: Sep. 2, 2013

(86) PCT No.: PCT/IL2013/050741
§ 371 (c)(1),
(2) Date: Mar. 3, 2015

(87) PCT Pub. No.: WO2014/037938
PCT Pub. Date: Mar. 13, 2014

(65) Prior Publication Data
US 2015/0254964 A1    Sep. 10, 2015

Related U.S. Application Data

(60) Provisional application No. 61/696,339, filed on Sep. 4, 2012.

(51) Int. Cl.
*G08B 23/00* (2006.01)
*G08B 21/24* (2006.01)
(Continued)

(52) U.S. Cl.
CPC ............ *G08B 21/245* (2013.01); *A61G 11/00* (2013.01); *G06F 19/327* (2013.01)

(58) Field of Classification Search
CPC ...... G08B 21/245; G08B 21/02; G08B 21/22; G08B 21/24; G06F 19/327;
(Continued)

(56) References Cited

U.S. PATENT DOCUMENTS 5,812,059 A    9/1998  Shaw et al.
6,727,818 B1 *  4/2004  Wildman ............ G06F 19/3418
                                                340/10.1
(Continued)

FOREIGN PATENT DOCUMENTS

WO    2008133495 A1    11/2008

OTHER PUBLICATIONS

ISR and written opinion of the international search authority for PCT/IL2013/050741, mailed on Mar. 27, 2014 (10 pages).

*Primary Examiner* — Anh V La
(74) *Attorney, Agent, or Firm* — Arent Fox LLP

(57) ABSTRACT

A method of monitoring neonatal incubator hygiene. The method comprises continuously monitoring a current hygiene level of a plurality of caregivers by detecting, per the caregiver, a plurality of personal hygiene events held during a monitoring period, identifying a care giving event during which a first of the plurality of caregivers is proximate to a preborn chamber of first of plurality of neonatal incubators, and generating an alert based on the current hygiene level when the care giving event is identified.

12 Claims, 13 Drawing Sheets

(51) Int. Cl.
*A61G 11/00* (2006.01)
*G06F 19/00* (2011.01)

(58) Field of Classification Search
CPC .............. G06F 19/3493; G06F 19/3418; A47K
2005/1218; G01S 5/02; A61G 11/00;
A61G 11/09; A61G 2210/30
USPC ........... 340/573.1, 540, 539.13, 286.07, 521,
340/573.4, 539.23, 539.12, 286.09;
702/19; 600/300, 22
See application file for complete search history.

(56) References Cited

U.S. PATENT DOCUMENTS

| | | | |
|---|---|---|---|
| 9,000,926 B2* | 4/2015 | Hollock | G08B 21/245 340/573.1 |
| 9,000,930 B2* | 4/2015 | Pelland | G01S 5/02 340/539.13 |
| 9,030,325 B2* | 5/2015 | Taneff | G06F 19/327 340/5.81 |
| 2001/0048027 A1 | 12/2001 | Walsh | |
| 2008/0131332 A1 | 6/2008 | Nguyen et al. | |
| 2010/0328443 A1 | 12/2010 | Lynam | |
| 2011/0169646 A1 | 7/2011 | Raichman | |

* cited by examiner

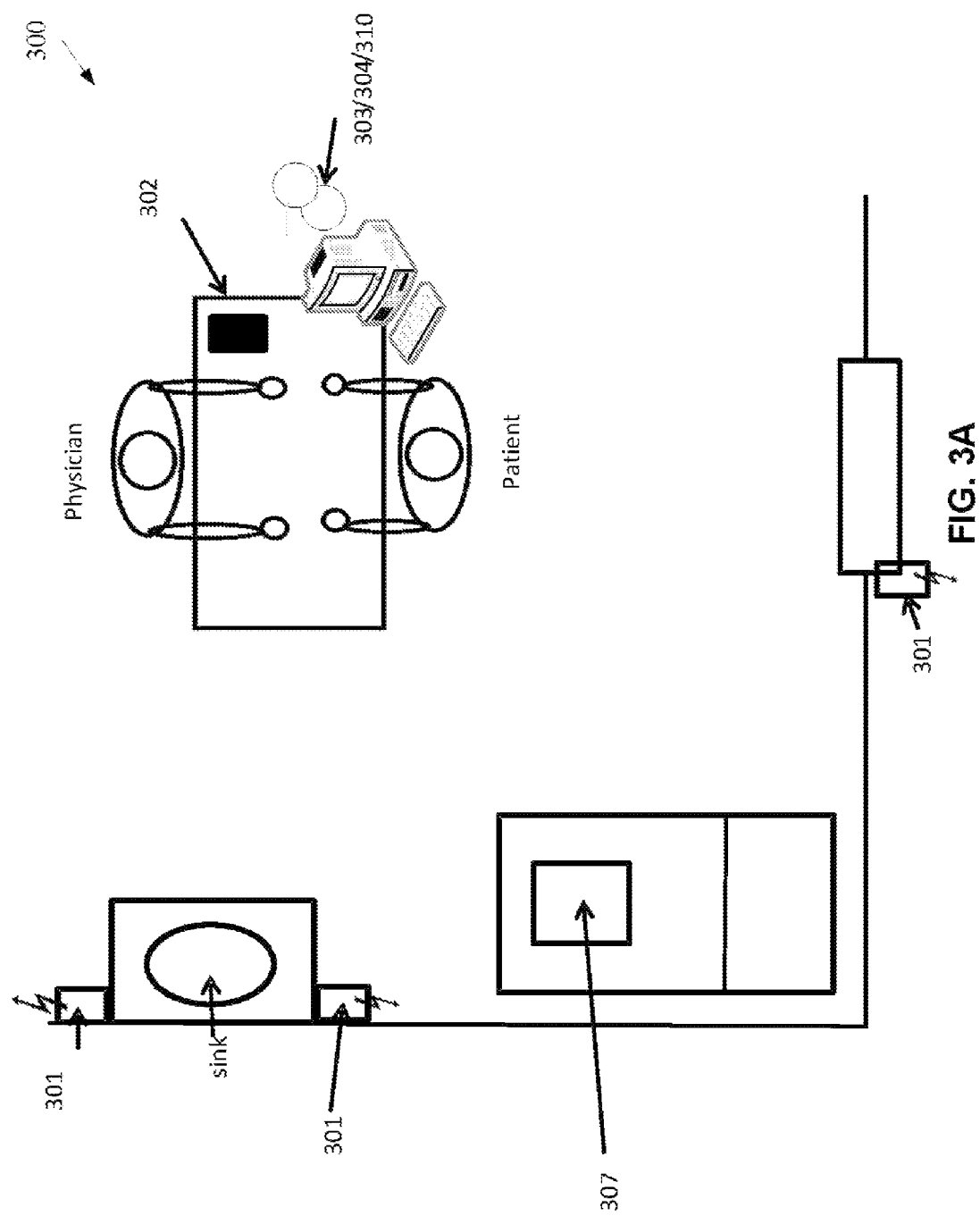

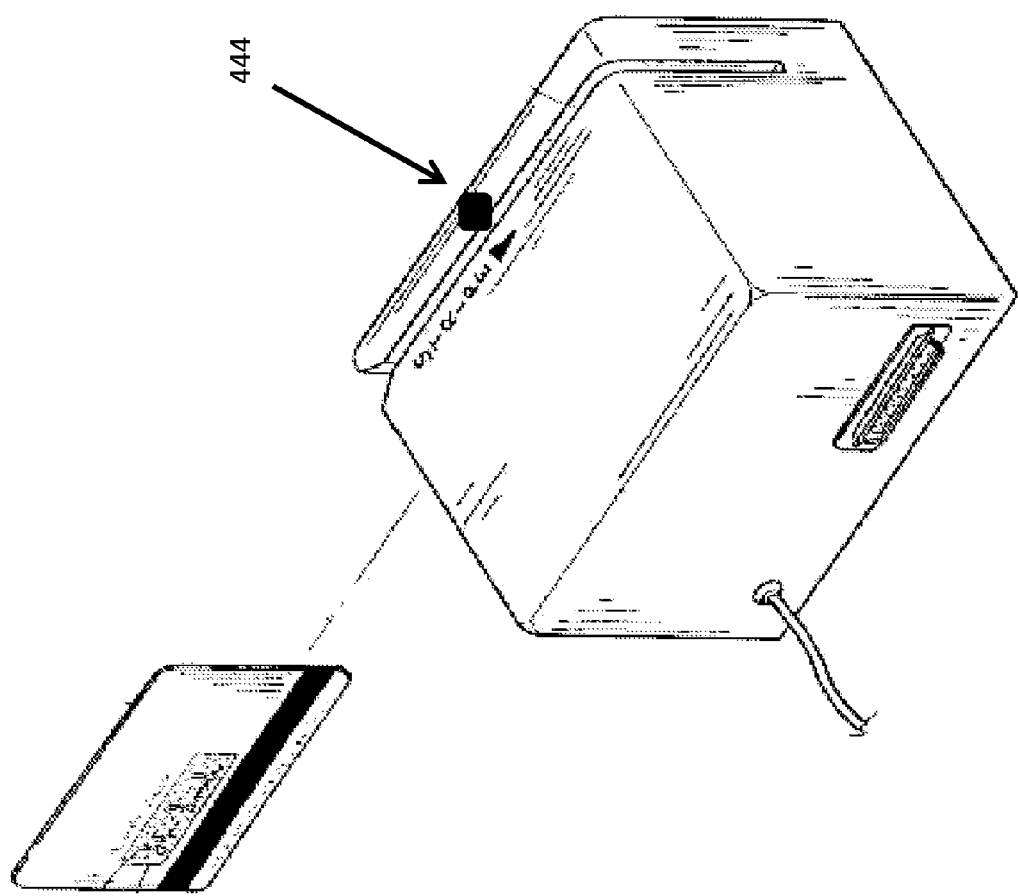

INFECTIOUS DISEASE SPREAD PREVENTION

CROSS REFERENCE TO RELATED APPLICATION

This application is a National Stage Entry of International Patent Application No. PCT/IL2013/050741, filed Sep. 2, 2013, which claims priority to U.S. Provisional Patent Application No. 61/696,339, filed Sep. 4, 2012, the disclosures of each of which are incorporated in their entirety herein by reference.

FIELD AND BACKGROUND OF THE INVENTION

The present invention, in some embodiments thereof, relates to a system and a method for monitoring hygiene compliance and/or status and, more particularly, but not exclusively, to a system and a method for monitoring personal hygiene compliance and/or status of users.

In various situations and environments, it is considered desirable to remind and/or to encourage people to perform personal hygiene tasks, such as washing their hands. Typical environments would include hospitals, care homes and hospices, where caregiver, such as nurses, doctors and therapists should wash their hands regularly, in particular when moving between treating different patients. Other environments where regular hand washing is required could include catering environments where food items are processed or at food processing facilities. It is necessary for people in such environments to take responsibility for their personal hygiene.

During the last years various devices have been developed in an attempt to improve the personal hygiene level of care takers and workers. This devices are designed to detects whether the user washes her hands or not and to output a sanitary signaling accordingly.

For example U.S. Pat. No. 5,952,924, filed on Dec. 4, 1997, describes a system for encouraging workers who work in a hygienically controlled area to wash their hands before exiting an associated sanitation area. Broadly, the present invention comprises a housing located in the sanitation area for receiving at least a portion of the hands of the worker. A detector is operatively associated with the housing. The detector detects whether or not the hands of the worker have recently been washed in response to the insertion of the hands of the worker into the housing. A communication media is also operatively associated with the detector for outputting one of a sanitary signaling media in response to the detection that the hands of the worker have been washed and an unsanitary signaling media in response to the detection that the hands of the workers have not been washed.

Another example is described in UK Patent Application No. GB 2417811A, filed on Aug. 12, 2005, that discloses hand washing detector device, suitable to be fitted to a person possibly on the hand or wrist, comprises a sensor for sensing a hand washing event and a timing module responsive to the sensor. The device may also include an alarm system wherein the timing module activates the alarm system when a first predetermined time limit is exceeded between hand washing events. The alarm may be audible, vibratory and/or visual and the sensor may detect the presence of water or any other chemical present during hand washing. The device may help in infection control by monitoring hand washing and reminding people to wash their hands regularly.

In addition, systems and methods for monitoring hygiene standards compliance in a certain environment have also been developed. For example, International Application No. PCT/EP2006/062895, filed on Jun. 2, 2006 describes a system and a method of monitoring hygiene standards compliance in a medical facility in which there is provided a surveillance network having a monitoring unit and a plurality of network units. There may additionally be provided a plurality of fixed network units. The monitoring unit, mobile network units and fixed network units are connected by way of a wireless personal area network (WPAN), in this case a ZigBee network. Identification signals are sent from the mobiles network units to the monitoring unit and the monitoring unit stores the identification signals in memory and generates a hygiene standards compliance profile for an individual associated with a particular mobile network unit. The hygiene compliance profile may provide information relating to the number of times that a particular individual washed their hands to information regarding the patients that that individual came into contact with over the course of a shift. Reports on the behavior of individuals or groups of individuals may be generated.

Another example is described in International Patent Application Pub. No. WO2010/026581, filed on Sep. 3, 2009, that describes a method for analyzing hygiene habits of a user. The method comprises attaching a personal hygiene monitor to the user, using the attached personal hygiene monitor for detecting a plurality of personal hygiene events related to the user, logging the plurality of personal hygiene events to allow configuring a user hygiene profile of the user, and estimating a hygiene level of one or more hygiene habits of the user according to the user hygiene profile.

SUMMARY OF THE INVENTION

According to some embodiments of the present invention, there is provided a method of monitoring neonatal incubator hygiene. The method comprises continuously monitoring a current hygiene level of a plurality of caregivers by detecting, per the caregiver, a plurality of personal hygiene events held during a monitoring period, identifying a care giving event during which a first of the plurality of caregivers is proximate to a preborn chamber of first of a plurality of neonatal incubators, and generating an alert based on the current hygiene level when the care giving event is identified.

Optionally, the identifying comprises updating the current hygiene level according to the care giving event; the generating comprises generating the alert if the current hygiene level indicates that no personal hygiene event was detected after a previously held care giving event.

Optionally, the identifying comprises receiving a signal indicative of a proximity to the preborn chamber from a beacon associated with the first neonatal incubator.

Optionally, the hygiene level is estimated according to a wearable sensor worn by the first caregiver.

Optionally, the care giving event is identified when a proximity of the first caregiver to one of the neonatal incubators is detected.

Optionally, the care giving event is identified when the hands of the first caregiver are detected in a chamber of the first neonatal incubator.

According to some embodiments of the present invention, there is provided a system of monitoring neonatal incubator hygiene in a ward. The system comprises a plurality of hygiene monitors to monitor continuously a current hygiene level of a plurality of caregivers by detecting a plurality of personal hygiene events related to the plurality of caregivers, a plurality of neonatal incubator sensors each identifies a care giving event during which a first of the plurality of caregivers is proximate to a preborn chamber of first of a plurality of neonatal incubators, and a central unit which receives data from a plurality of hygiene monitors and the plurality of neonatal incubator sensors to generate an alert if the current hygiene level is below a threshold when a respective the care giving event is identified.

Optionally, each neonatal incubator sensor detect an insertion of a hand into a chamber of a respective the neonatal incubator as the care giving event.

Optionally, each hygiene monitor comprises an image sensor and detects the personal hygiene event by an analysis of a plurality of images captured by the image sensor.

Optionally, at least some of the plurality of hygiene monitors are stationary and disposed to image at least a portion of a medical treatment area wherein the plurality of neonatal incubators are located.

According to some embodiments of the present invention, there is provided a system of monitoring hygiene of a caregiver in a medical treatment venue. The system comprises a usage sensor which continuously monitor usage of at least one personal hygiene device in a medical treatment venue to identify first timing of a personal hygiene event, a treatment session interchange detecting unit which detects second timing of a treatment session initiation event during which a new patient is about to participate in a new treatment session at the medical treatment venue, and a current hygiene module which matches between the first and second timings to determine at least one of whether to trigger the presentation of an alert and whether to prevent the initiation of the new treatment session.

Optionally, the treatment session interchange detecting unit detects the treatment session initiation event by monitoring a member of a group consisting of: a room door, a patient chair, a patient bed, and an imaging modality post.

Optionally, the treatment session interchange detecting unit detects the treatment session initiation event by monitoring an operation of a patient identification (ID) reader device.

More optionally, the patient ID reader is a card reader; wherein each treatment session initiation event is detected by detecting a card swipe.

More optionally, the current hygiene module operates a mechanical barrier which prevents and allows the operation according to the match.

Optionally, the system further comprising an interface which receives from a software module a plurality of signals each indicative of a treatment session initiation; wherein the treatment session initiation event are detected by an analysis of the plurality of signals.

More optionally, the software module is selected from a group consisting of a customer relationship management (CRM) software module and/or electronic medical records (EMR) software module, and a patient queue software module.

Optionally, the treatment session interchange detecting unit detects ID reader is a card reader.

According to some embodiments of the present invention, there is provided a method of monitoring hygiene of a caregiver in a medical treatment venue. The method comprises continuously monitoring usage of at least one personal hygiene device in a medical treatment venue, identifying a first timing of a personal hygiene event according to the monitoring, detecting second timing of a treatment session initiation event during which a new patient is about to participate in a new treatment session at the medical treatment venue, matching between the first and second timings, and determining at least one of whether to trigger the presentation of an alert and whether to prevent the initiation of the new treatment session.

According to some embodiments of the present invention, there is provided a method of monitoring infections in a medical treatment area. The method comprises logging in a dataset location information of a plurality of persons in a monitored area during a monitoring period of at least several hours, receiving an identifier of at least one infectious person from the plurality of persons or at least one infectious location in the monitored area and an estimated infection time, reviewing the dataset to identify a plurality of spatiotemporal encounters held after the estimated infection time between the at least one person and a group of the plurality of persons or a plurality of spatiotemporal arrivals of members of the group to at least one infectious location, assembling a list of members of the group, and outputting the list.

Optionally, the monitoring period is of at least 24 hours.

Optionally, the reviewing comprises identifying a plurality of additional spatiotemporal encounters between members of the group and a second group of the plurality of persons after the estimated infection time; the assembling comprises adding members of the second group to the list.

More optionally, the reviewing comprises identifying a plurality of further additional spatiotemporal encounters between members of the second group and a third group of the plurality of persons after the estimated infection time; the assembling comprises adding members of the third group to the list.

Optionally, the logging further comprising associating a plurality of personal location indicators with the plurality of persons, receiving a current location from each personal location indicator a plurality of times during the monitoring period and updating the location information in the dataset accordingly.

According to some embodiments of the present invention, there is provided a system of monitoring infections in a monitored area. The system comprises a database which stores dataset location information of a plurality of persons in a medical treatment area during a monitoring period of at least 24 hours, an input unit which receives an identifier of at least one infectious person from the plurality of persons or at least one infectious location in the monitored area and an estimated infection time, a detecting module which reviews the dataset to identify a plurality of spatiotemporal encounters held after the estimated infection time between the at least one person and a group of the plurality of persons or a plurality of spatiotemporal arrivals of members of the group to at least one infectious location and assembles a list of members of the group, and an output module which outputs the list.

Optionally, the system further comprises a plurality of personal location indicators which are associated with the plurality of persons and set to transmit a current location and a plurality of location readers which receives the current location from each personal location indicator and updates the location information in the dataset accordingly.

According to some embodiments of the present invention, there is provided a hygiene monitoring name tag. The tag comprises a body, an attachment element which is set to attach the body to a clothing article worn by a wearer, a presentation surface, mounted on the body for displaying the identity of the wearer for others to view, an image sensor which captures an image sequence and mechanically connected to the body, and a processing unit which is mechanically connected to the body, receives the image sequence and identifies, based on image processing analysis, a plurality of personal hygiene events related to the wearer.

According to some embodiments of the present invention, there is provided a method of monitoring hygiene of a person using a monitoring name tag. The method comprises attaching to a hygiene monitoring name tag device having an image sensor to a clothing article worn by a wearer, capturing a plurality of images using the image sensor, detecting at least one personal hygiene event of the wearer, during a monitoring period, according to an image processing analysis of at least one image of the plurality of images, detecting at least one of a potential contamination venue and a potential contamination event pertaining to the wearer, during a monitoring period, using the hygiene monitoring name tag device, and generating a notification based on a combination of the at least one personal hygiene event and at least one of the potential contamination venue and the potential contamination event.

Optionally, the detecting at least one personal hygiene event of the wearer comprises detecting a quality level of the at least one personal hygiene event, notification is set according to the quality level.

Optionally, the image processing is performed by identifying a label attached to a hygiene related object.

Optionally, the detecting at least one of a potential contamination venue and a potential contamination event pertaining to the wearer is performed by using the hygiene monitoring name tag device to capture a video sequence and based on image processing analysis of the video sequence.

Optionally, the image processing is performed by identifying a label attached to an object in the potential contamination venue.

Optionally, the image processing is performed by identifying an illumination pattern used to illuminate the potential contamination venue.

According to some embodiments of the present invention, there is provided a method of monitoring a care giving location. The method comprises continuously illuminating a plurality of care giving locations, each in a different geographical location, with a plurality of uniquely coded illuminations during a monitoring period, continuously monitoring a current hygiene level of a plurality of caregivers during the monitoring period, identifying a care giving event during which a first of the plurality of caregivers is proximate to a first of the plurality of care giving locations, and generating an alert based on the current hygiene level when the care giving event is identified.

According to some embodiments of the present invention, there is provided a system of monitoring neonatal incubator hygiene in a neonatal incubator. The system comprises a usage monitor which detects usage in a personal hygiene device by a caregiver, a neonatal incubator sensor which identifies a care giving event during which a caregiver is proximate to a preborn chamber of a neonatal incubator, and a controller which receives data from the usage monitor and the neonatal incubator sensor to generate an alert according to a match between the usage and the care giving event.

According to some embodiments of the present invention, there is provided a method of detecting a personal hygiene event. The method comprises measuring a distance between a hand worn personal hygiene monitoring device having an accelerometer and a proximity sensor located in proximity to a hand hygiene device selected from a group consisting of a tap, a liquid dispenser, a powder dispenser, a soap stand and a towelette dispenser, when the distance is below a certain value, scoring at least one characteristic of a movement of the hand worn personal hygiene monitoring device in proximity to the proximity sensor by analyzing an output of the accelerometer, and outputting the score.

Optionally, the method further comprises generating a notification based on the score.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A is a schematic illustration of a system for monitoring the hygiene of a caregiver in a medical treatment venue in which patients sequentially come and go, for example a clinic and/or a physician office, according to some embodiments of the present invention;

FIG. 3B is a schematic illustration of a card reader with a mechanical barrier that is operated according the detection and/or the failure to detect one or more personal hygiene events, according to some embodiments of the present invention;

DESCRIPTION OF EMBODIMENTS OF THE INVENTION

Figure 1A:
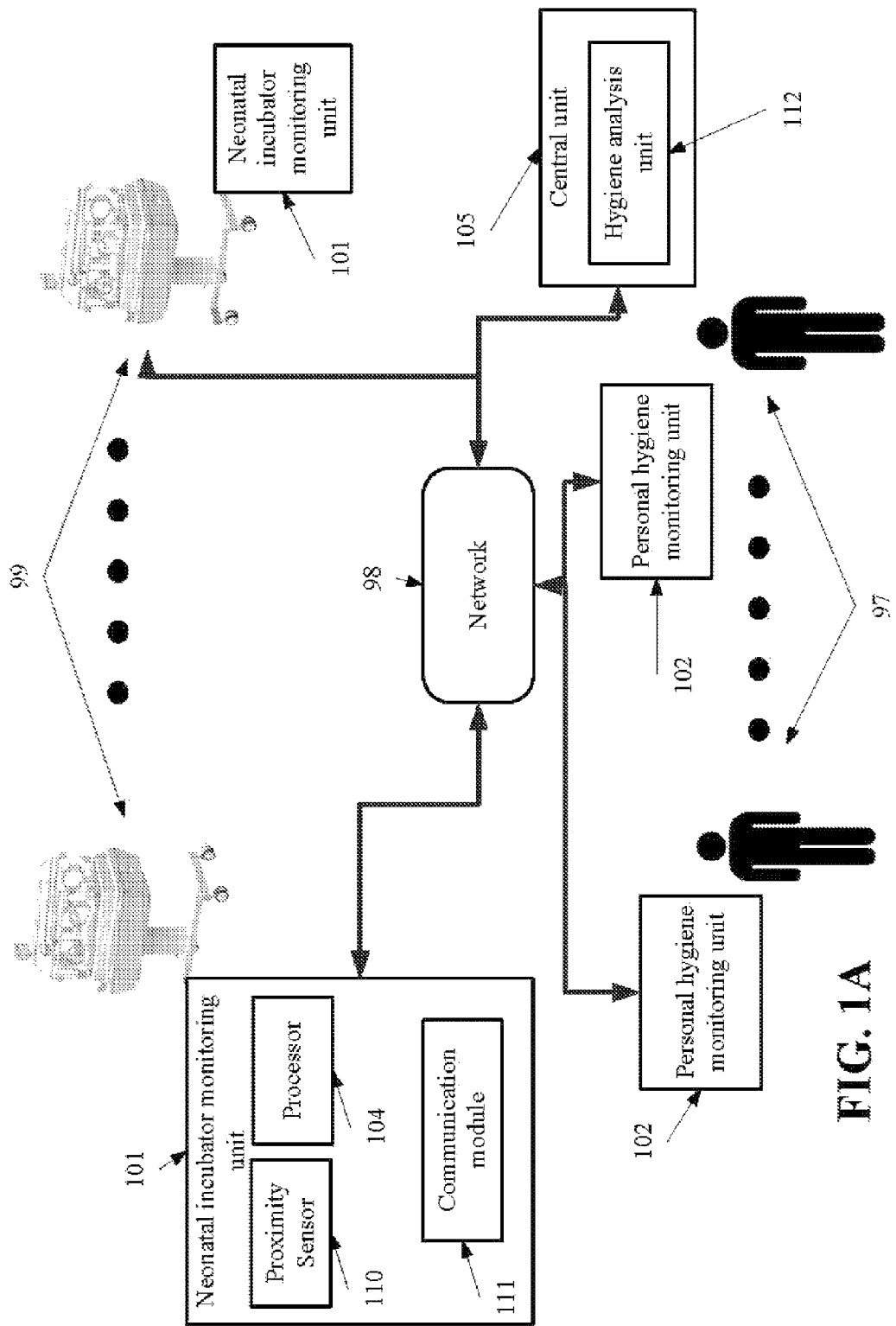
FIG. 1A is a schematic illustration of a system of monitoring neonatal incubator hygiene in one or more babies or premature babies wards by simultaneously monitoring a hygiene level of a plurality of caregivers and babies and/or premature babies care events by the caregivers, according to some embodiments of the present invention.

The present invention, in some embodiments thereof, relates to a system and a method for monitoring hygiene compliance and/or status and, more particularly, but not exclusively, to a system and a method for monitoring personal hygiene compliance and/or status of users.

According to some embodiments of the present invention, there are provided methods and systems of monitoring hygiene of caregivers in one or more baby wards and/or premature baby wards by continuously monitoring a current hygiene level of a plurality of caregivers and detecting care giving events at preborn chambers of a plurality of neonatal incubators. The methods and systems are set to activate a notification, an alert before and/or during a care giving event when the current hygiene level of the respective caregiver is not sufficient. The monitoring may be performed by a plurality of personal hygiene monitors which are worn or otherwise placed to track personal hygiene events of a plurality of patients.

According to some embodiments of the present invention, there are provided methods and systems of monitoring hygiene of a caregiver that sequentially receives a plurality of patients, usually ambulatory, in the same medical treatment venue, for example a clinic. The methods and systems are based on one or more usage sensors which continuously monitor usage of personal hygiene device(s), such as dispensers and/or towelettes in the medical treatment and one or more treatment session interchange detecting units which detect when a new patient is about to participate in a new treatment session at the medical treatment venue, for example enters the venue, sits in a chair, poses to be imaged by an imaging modality and/or the like. Usage sensors which monitor towelette dispenser usage may be based on pressure sensors, accelerometer(s) and/or angle detectors which are mounted on a lid of the towelette dispenser (or in proximity thereto) for detecting opening. Optionally, the towelette dispenser includes a closing assurance mechanism that assures that the lid of the towelette dispenser is closed after usage to avoid false positive and/or negative identification. The closing assurance mechanism may be based on a spring and/or another withdrawing element and/or movement bounding element.

A treatment session interchange detecting unit, may be, for example, an image sensor, a movement sensor, a proximity sensor, a unit that detects when a patient ID reader, such as a card reader, is used, and/or a unit that detects new patient by monitoring management software module, for example client queue software module and/or an electronic medical records (EMR) software module. The output of these units is optionally forwarded to a current hygiene module, for example a module installed in the desktop of the caregiver, which decides accordingly whether to trigger the presentation of an alert and/or to prevent the initiation of a treatment session.

Optionally, the alert is presented on a display. Optionally, the initiation of the treatment session is prevented by blocking the usage of a management software module and/or the patient ID reader.

According to some embodiments of the present invention, there are provided methods and systems of monitoring infections in a monitored area by logging, in a dataset, location information of a plurality of persons in a monitored area during a monitoring period several hours or more, for example 24 hours and analyzing the dataset to identify spatiotemporal encounters, held after a certain estimated infection time, between one or more infectious persons and a group selected form a crowd of monitored persons and/or spatiotemporal arrivals of members of such a group to one or more locations identified as infectious. This analysis allows assembling a list of potentially contaminated patients and/or locations (e.g. locations which contaminated patients may be found and/or visited). The systems and method may be used for real time identification of the contaminated patients and/or locations, for example in response to the identity of person(s) and/or location(s) identified as infectious.

The location information may be gathered by attaching to each person a personal location indicator and monitoring continuously (e.g. sequentially, iteratively, and/or randomly in a sufficient rate during a continuous monitoring period) the location of the plurality of personal location indicators, optionally using a gird of readers that is distributed in the monitored area.

According to some embodiments of the present invention, there are provided a hygiene monitoring name tag that includes sensors and/or location indicators of monitoring hygiene of a person and methods of using thereof. These embodiments allows using a hygiene monitoring name tag to monitor current hygiene level and/or to generate a hygiene habits score by detecting personal hygiene events and the presence of the monitored wearer in a potential contamination venue and/or the participation thereof in a potential contamination event.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1A, which is a schematic illustration of a system 100 of monitoring neonatal incubator hygiene in one or more babies and/or premature babies wards by simultaneously monitoring a hygiene level of a plurality of caregivers 97 and babies and/or premature babies care events by the caregivers, according to some embodiments of the present invention. As used herein, neonatal incubator may be any crib, open and/or closed cradles, chambers, and/or a bed for a baby.

The system 100 includes a plurality of neonatal incubator monitoring units 101 which are installed to monitor neonatal incubator 99 and a plurality of personal hygiene monitoring units 102.

Figure 1D:
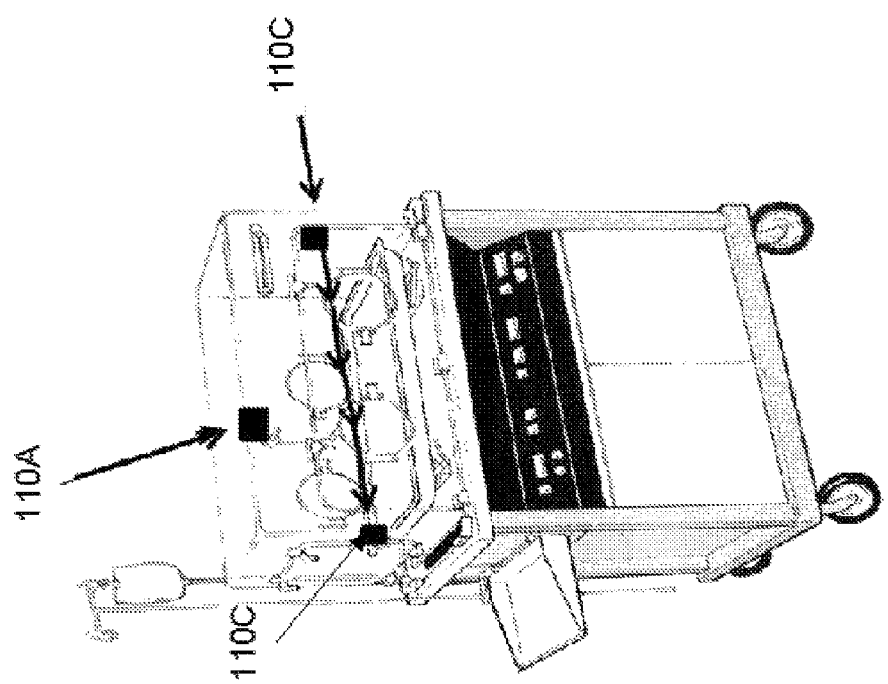
FIGS. 1B-1D are schematic illustrations of neonatal incubator with different sensors for detecting hands of a caregiver, according to some embodiments of the present invention.
Figure 1C:
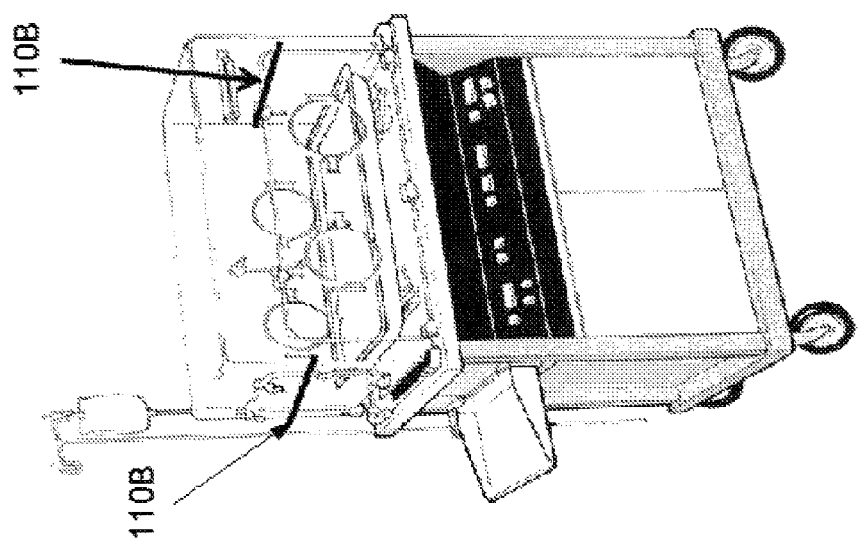
Figure 1B:
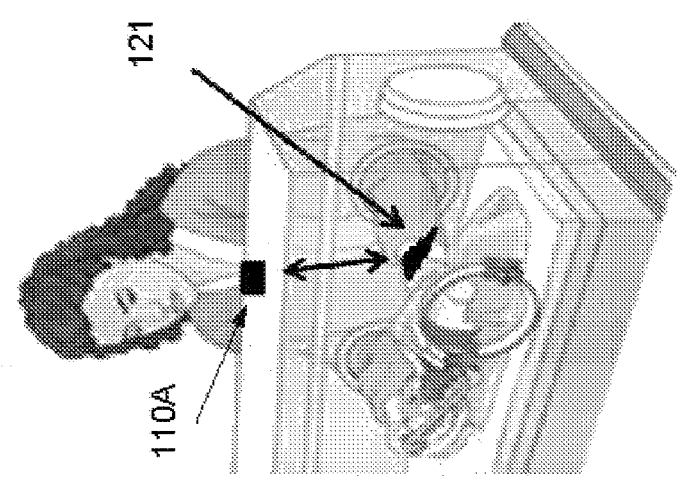

The neonatal incubator monitoring units 101 optionally comprises a proximity sensor 110 to detect a care giving event, for example when a caregiver is located in proximity to a respective neonatal incubator. The proximity sensor 110 may be a sensor that detects a care giving event when hands are inserted into baby chamber of the respective neonatal incubator. For example, as shown at FIG. 1B, if the caregiver wears a personal hygiene monitor 121 that is integrated in a bracelet, for example as described in as defined in International Patent Application Pub. No. WO2010/026581, the proximity sensor 110A may be a receiver unit that detects signals from the personal hygiene monitor. In another example, as shown at FIG. 1C, the proximity sensor 110 may be volume detectors which identify a change in the incubator chamber. In another example, as shown at FIG. 1D, the proximity sensor 110 may be an optical sensor that detects when a transmission from a transmitting element is blocked by a hand placed in the incubator chamber. The proximity sensor 110 may be a movement sensor, for example an optical sensor, such as a CMOS based sensor or a CCD based sensor that detects a movement in the baby chamber and/or in the hand apertures thereof. The proximity sensor may be a volume detector, for example and acoustic and/or ultrasonic sensor. The proximity sensor may be a radar type sensor that detects radio frequency (RF) and/or microwave (MW) signals' reflection to identify hands and/or hand movement. Piezoelectric sensors may also be used to detect pressure change on a mattress of the baby chamber. The neonatal incubator monitoring unit 101 further includes a processor 104 for generating a detection signal based on the outputs of the proximity sensor and optionally a communication module 111, such as a WLAN module, for example a Wi-Fi module that forwards the detection signal to a central unit 105, optionally wirelessly. The central unit 105 may be implemented on a network node of a network 98, for example a computing unit, such as a desktop, a laptop, a tablet, a Smartphone, and/or any other processor based unit with a respective communication capabilities. The communication between the communication module 104 and the central unit 105 may be wired.

Additionally or alternatively, the neonatal incubator monitoring units 101 comprises a beacon module that signals a geographical location and/or neonatal incubator identifier to indicate to the personal hygiene monitoring units 102 when they are in proximity to the respective neonatal incubator. For example, the beacon module may be a transmitter that transmits an identifying signal, such as an RF signal, an infrared (IR) signal, and/or an ultrasonic signal with an encoded unique identify, for example RF identifier (RFID) transmitter. Optionally, in such embodiments, the personal hygiene monitoring units 102 includes a communication module, such as a WLAN module, for example a Wi-Fi module that forwards a detection signal that is similar to the above detection signal to the central unit 105, optionally wirelessly. This allows the central unit 105 to identify a care giving event and to generate alert, if needed, accordingly. Additionally or alternatively, each neonatal incubator monitoring units 101 is illuminated by light encoded in a unique code that signals a geographical location and/or neonatal incubator identifier to indicate to the personal hygiene monitoring units 102 when they are in proximity to the respective neonatal incubator. For example, an illuminator such as an IR LED may be placed to illuminate with an identifying signal, for example on top of the neonatal incubator. Optionally, in such embodiments, the personal hygiene monitoring units 102 includes an image sensor, such as a CMOS based sensor, which captures the illumination and translates it to extract the geographical location and/or the neonatal incubator identifier. This allows identifying a care giving event generating alert, if needed, accordingly. The image sensor and/or another image sensor may be used for detecting a care event by image analysis, for example as described below.

Additionally or alternatively, in such embodiments, the personal hygiene monitoring units 102 locally generates the alert. In such an embodiment, the neonatal incubator monitoring unit 101 identifies when a caregiver is about to give and/or giving a treatment to a newborn in a neonatal incubator and if the hygiene status of this caregiver is sufficient for providing the treatment. This allows alerting the caregiver and/or a third party (i.e. by sending a message) if the hygiene status of the caregiver is insufficient. The identification may be performed by correlating between data gathered by the personal hygiene monitoring units 102 regarding current hygiene status and data gathered from and/or using the neonatal incubator monitoring units 101, for example location based data.

Additionally or alternatively, in such embodiments, each neonatal incubator monitoring unit 101 is wirelessly or wirely connected to a sensor that monitors the usage of a certain personal hygiene device, for example a certain personal hygiene device which is attached to a respective neonatal incubator and/or located in proximity thereto. In such embodiments, each one of the neonatal incubator monitoring units 101 verifies that a caregiver uses the personal hygiene device before she is about to give and/or giving a treatment to a newborn in a neonatal incubator and if the hygiene status of this caregiver is sufficient for providing the treatment. This allows alerting the caregiver and/or a third party (i.e. by sending a message) if the hygiene status of the caregiver is insufficient. The identification may be performed by correlating between data gathered by sensor that monitors the certain personal hygiene device 101 and data gathered from and data gathered by the respective neonatal incubator monitoring unit 101, for example time based data. In such embodiments, personal hygiene monitoring units 102 may not be used.

The personal hygiene monitoring units 102 are optionally units, which are designed to monitor hygiene habits of the caregivers and/or a current hygiene status of the caregivers. A personal hygiene monitoring unit 102 may be placed in a bracelet and/or in any other wearable item that is worn by each one of the caregivers, for example as described in International Patent Application Pub. No. WO2010/026581, which is incorporated herein by reference. The personal hygiene monitoring units 102 optionally forwards data pertaining to hygiene events pertaining to a monitored caregiver to the central unit 105. As used herein, a personal hygiene event means any event that has an effect on the hygienic level of a user. Such personal hygiene event may be hygienic habits like using disposable tissues, washing hands, disinfecting hands using a disinfect agent, such as alcohol, taking showers, replacing medical safety accessories, such as latex gloves, wearing a face mask, such as a surgical mask, being in a hygiene event related location, such as a shower, a proximity to sink, and/or a disinfecting agent dispenser, and the like. The personal hygiene event may be detected by sensors on the personal hygiene monitoring unit 102, for example an optical sensor, a proximity sensor, and/or a movement sensor and/or by external sensors located in hygiene related sites, such as dispensers and/or the like.

In some embodiments of the present invention, the central unit 105 includes a hygiene analysis unit 112 that manages a plurality of user profiles. Each user profile logs personal hygiene events which are related to a certain caregiver, for example a nurse, a physician, a paramedic, a therapist, and a member of the emergency medical service, a parent, and/or any guardian. Optionally, each user profile is associated with a user identifier (ID), a list that documents the personal hygiene events, which are related to the user, and a current hygiene score that reflects an estimated evaluation of the hygiene habits of the user, optionally calculated as described in International Patent Application Pub. No. WO2010/026581, which is incorporated herein by reference. The user profiles are designed to store logged personal hygiene events which are related to the user.

In use, the system 100, for example the central unit 105 identifies when a caregiver is about to give and/or giving a treatment to a newborn in a neonatal incubator and if the hygiene status of this caregiver is sufficient for providing the treatment. This allows alerting the caregiver and/or a third party if the hygiene status of the caregiver is insufficient. The identification may be performed by correlating between data gathered by the personal hygiene monitoring units 102 regarding current hygiene status and data gathered from and/or using the neonatal incubator monitoring units 101, for example location based data. Optionally, the central unit 105 verifies that a caregiver washes hands and/or otherwise disinfect hands between treatment(s) he gives one newborn in one neonatal incubator and another newborn in another neonatal incubator.

It should be noted that the functionalities of the central unit may be separately performed by the personal hygiene monitoring units 102 for different caregivers. In such embodiments, the personal hygiene monitoring units 102 monitor the location and/or activity of a related caregiver, for example a wearing caregiver, for instance by gathering location data from beacon modules as described above. In such embodiments, alerts may be presented by a current hygiene module in the personal hygiene monitoring unit 102, for example a speaker and/or one or more light-emitting diodes (LEDs).

Figure 2:
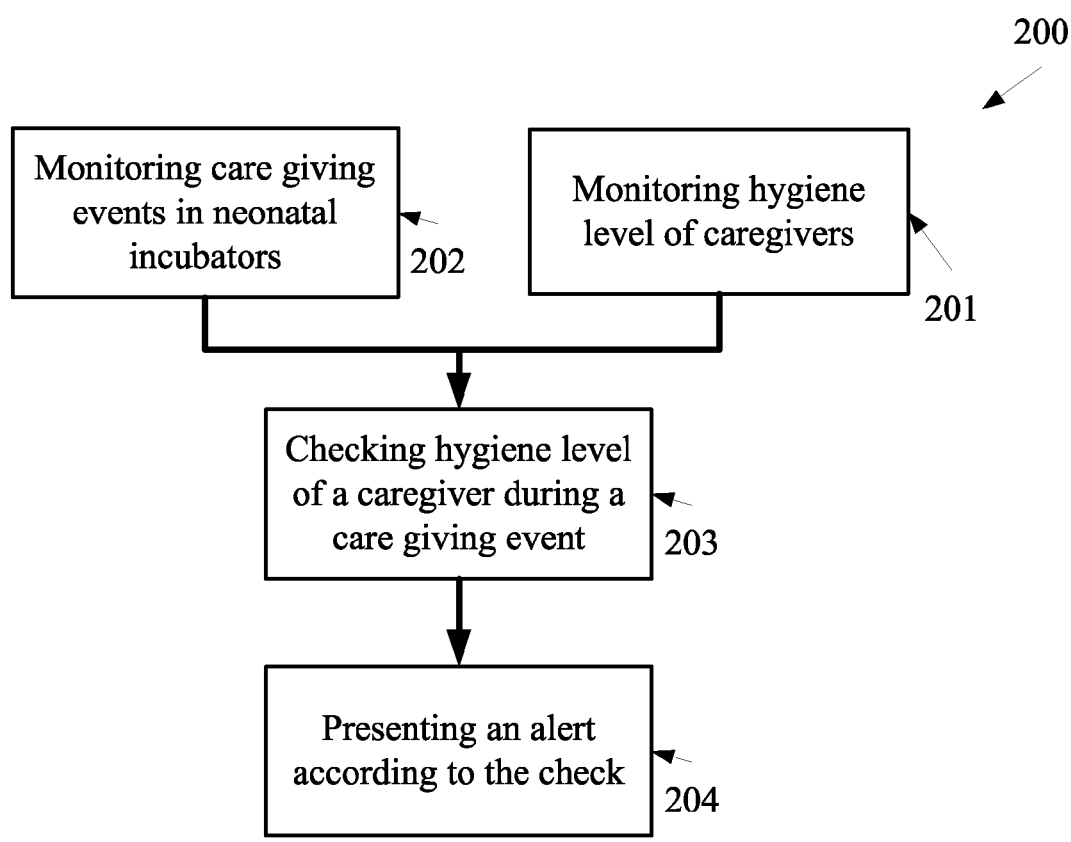
FIG. 2 is a flowchart of a method of monitoring neonatal incubator hygiene, for example using the system in FIG. 1A, according to some embodiments of the present invention.

For example, reference is now made to FIG. 2, which is a flowchart of a method of monitoring neonatal incubator hygiene, for example using the system 100 in FIG. 1A, according to some embodiments of the present invention.

First, as shown at 201, a hygiene status, also referred to as a hygiene level, of a plurality of caregivers is monitored during a monitoring period, for example one or more shifts. In addition, as shown at 202, care giving events during which one or more caregivers are in proximity to one of the neonatal incubators and/or having their hands therein are monitored during the monitoring period. When a care event is detected, for example when the proximity of a certain caregiver of the caregivers 97 to one of the neonatal incubators is detected, the hygiene status of the certain caregiver is checked, as shown at 203. As shown at 204, if the hygiene status of the proximate and/or giving treatment caregiver(s) is below a threshold, an alert is presented, for example sounded and/or otherwise indicated.

Reference is now made to FIG. 3A, which is a schematic illustration of a system 300 for monitoring the hygiene of a caregiver in a medical treatment venue in which patients sequentially come and go, for example a clinic and/or a physician office, according to some embodiments of the present invention. The medical treatment venue is optionally a doctor's surgery or doctor's office, namely a place where a physician, such as a general practitioner (GP) or a specialist receives and treats patients, for example give ambulatory care. It should be noted that the patients may not wear any identification means and therefore the identification of the initiation of treatment sessions requires a device that identifies new patients without having preliminary information thereabout.

The system 300, referred to herein as a clinic monitoring hygiene system 300, includes one or more usage sensors 301 which continuously monitor usage of a personal hygiene device, such as a cleaning material dispenser in the monitored medical treatment venue, for example alcohol dispenser and/or soap dispenser. The usage sensor 301 monitors and optionally logs the timing of personal hygiene events, such as hand washing events and/or dispenser usage events. In such embodiments, the usage sensor 301 may include an optical sensor to detect by processing in real time images depicting a volume in front of a personal hygiene device, such as a tap and/or a dispenser, a proximity sensor, such as a volume detector to detect the hands of the caregiver in a certain volume, for example a hand drying device and/or a chamber around the tap, a pressure sensor which detects caretaker actions, for example opening a tap, and/or any other sensor.

Optionally, the usage sensor 301 is connected to a processor based unit 303 which hosts a management module 304, for example a desktop, a laptop, a Smartphone, and/or a tablet of the physician. The management module 304 receives and optionally logs usage indications from usage sensor 301, for example when a tap and/or a dispenser are being used.

The clinic monitoring hygiene system 300 further includes a treatment session interchange detecting unit 302 which detects the timing of treatment session initiation events, namely events during which patients enters the medical treatment venue. Optionally, the interchange detecting unit 302 is installed in or in connection with a Patient ID reader that is used to identify patients by reading identification data from a card-shaped storage medium and/or any other storage medium, for example a card reader, and an RFID reader. The interchange detecting unit 302 estimates that a new treatment session starts whenever a new ID is identified by the Patient ID reader. The interchange detecting unit 302 may be a software module that receives information about the identification of a new patient, for example when a respective customer relationship management (CRM) and/or electronic medical records (EMR) software is updated.

The data is forwarded to the management module 304, for example wirelessly, for instance using RF communication, such as Wi-Fi communication. In one example, the interchange detecting unit 302 includes a movement sensor that detects the movement of a card in proximity to a card reader. In such embodiments, it is possible to identify when a new patient is received by the caregiver without accessing data from CRM and/or EMR software and/or requiring from the caregiver to perform a designated reporting action.

Additionally or alternatively, the interchange detecting unit 302 is installed in or in connection with a billing unit that is used to bill patients for a treatment session. Whenever a billing is identified, a treatment session for a new patient is estimated to be concluded and/to initiated by the physician.

Additionally or alternatively, the interchange detecting unit 302 comprises a presence sensor that detects whenever a new patient enters the medical treatment venue, for example an optical sensor and/or a proximity sensor, for example as defined above.

Optionally, the presence sensor is a pressure sensor that is placed on a patient chair and/or patient bed, for example as shown at 307. Optionally, the presence sensor is a sensor used to detect when a medical modality is used, for example an imaging device and/or a surgical device. Additionally or alternatively, the interchange detecting unit 302 includes a button that allows the physician to indicate when a treatment session starts and/or ends.

The system further includes a current hygiene module 310 that matches between the timings of a usage event, for example personal hygiene event(s) of the caregiver in the medical treatment venue and the timings of the treatment sessions to determine whether to trigger an alert or not. If the personal hygiene event(s) do not indicate that the caregiver performed a personal hygiene event, for example washed hands, during an interlude between treatment sessions, for example before a new treatment session starts, than an alert may be generated, for example a vocal and/or a visual alert. Optionally, the current hygiene module 310 forwards a notification about the alert and/or the timing data to a third party. Optionally, the current hygiene module 310 forwards the data to a hygiene analysis unit that manages a caregiver profile. The caregiver profile logs personal hygiene events, which are related to a certain caregiver.

Optionally, the caregiver profile is associated with a user identifier (ID), a list that documents the personal hygiene events, which are related to the caregiver, and a current hygiene score that reflects an estimated evaluation of the hygiene habits of the caregiver, optionally calculated as described in International Patent Application Pub. No. WO2010/026581, which is incorporated herein by reference. Optionally, the current hygiene score is made available to patients, for example in a designated webpage and/or presented on a display at the clinic.

Optionally, the clinic monitoring hygiene system 300 includes and/or connected to a queue management unit. For example, the interchange detecting unit 302 receives a notice from a queue management unit whenever a new patient is designated to enter the medical treatment venue of the caregiver.

As described above, the system 300 may be connected to CRM and/or EMR software and/or to a patient ID reader, for example a card reader. Optionally, the registration and/or reception of a new patient, for example by the CRM and/or EMR software and/or the activation of the Patient ID reader is conditioned by the current hygiene status and/or the detection and/or absence of the detection of a personal hygiene event, for example washing hands event. In such embodiments, the caregiver is forced to ensure his personal hygiene before she receives a new patient. Optionally, the conditioning is based on a message that is sent from the system 300 to the CRM and/or EMR and/or a queue management unit and/or the Patient ID reader software. This CRM and/or EMR and/or the queue management unit and/or the Patient ID reader software condition the receiving of and/or the calling to a new patient in receiving such a message. Optionally, the conditioning is enforced using a mechanical barrier that is placed to prevent from the caregiver to swipe an ID card and/or any other identification means using the Patient ID reader in the absence of a detection of a personal hygiene event. The mechanical barrier may be a box that contains the reader, a mechanical arm and/or a protrusion that switches between a closing state to an open state and/or the like. For example, FIG. 3B depicts exemplary card reader with a mechanical barrier 444 that blocks a card swiping area in a blocking mode and does not block the card swiping area in a cleared mode, when personal hygiene event is detected, for example as described above and below.

Figure 3C:
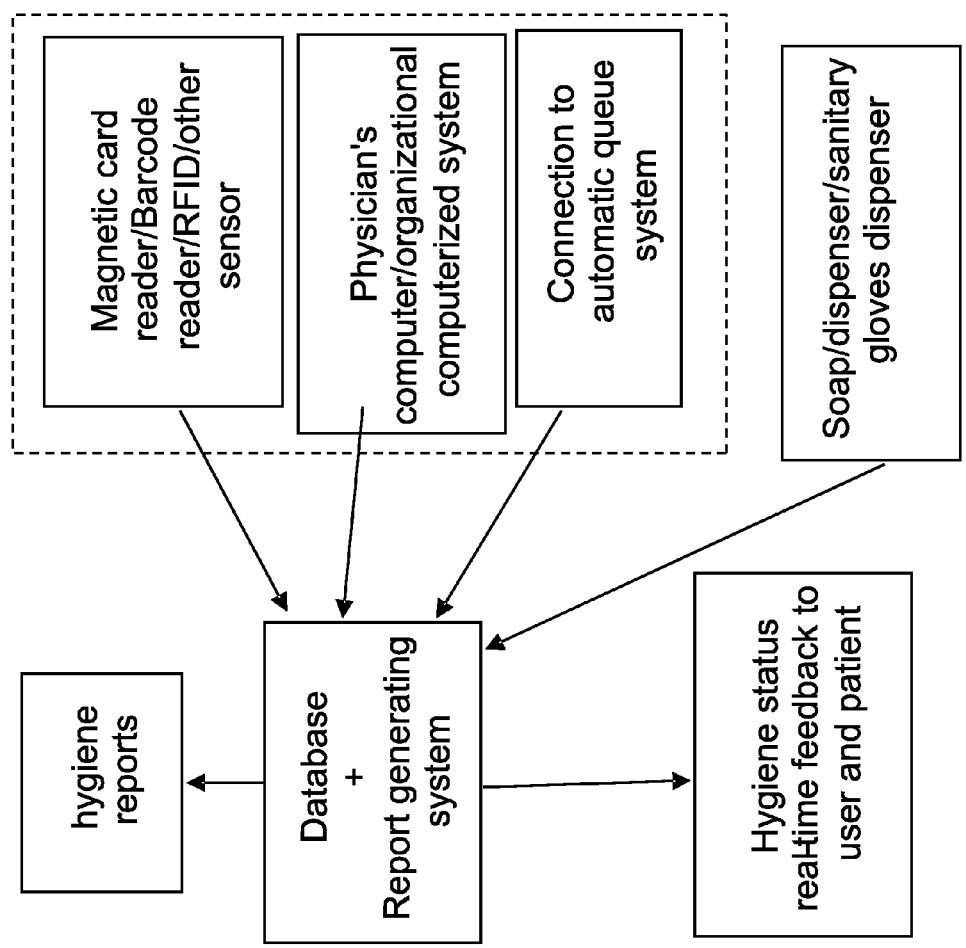
FIG. 3C is a schematic illustration of an exemplary flow of data that facilitates the generation of hygiene reports, the calculation of hygiene score(s), and/or providing real time hygiene statuses, according to some embodiments of the present invention.

For example, FIG. 3C depicts exemplary flow of data wherein data from Patient ID reader, EMR software, queue management system, and personal hygiene event sensors is forwarded to be stored in a database, facilitating the generation of hygiene reports, the calculation of hygiene score(s), and/or providing real time hygiene statuses.

Figure 4:
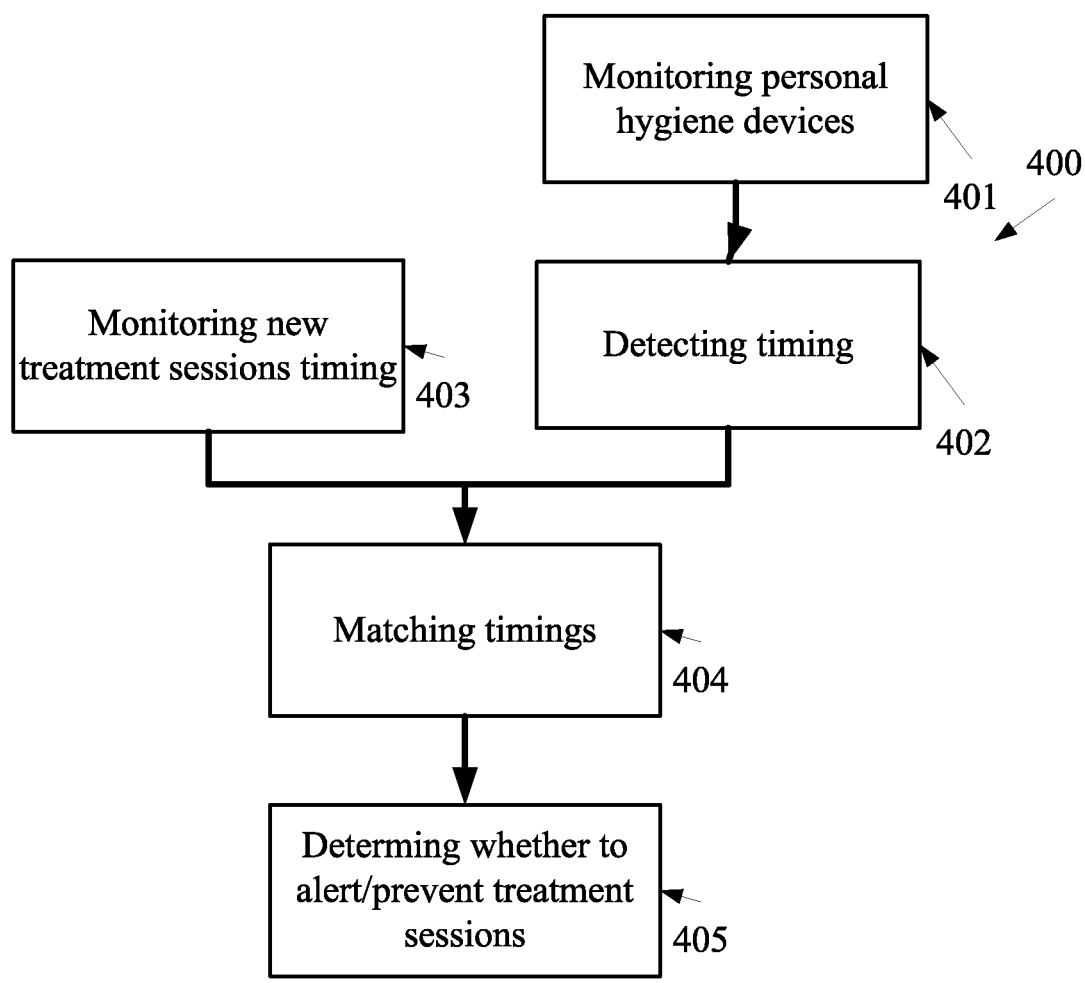
FIG. 4 is a flowchart of an exemplary method of monitoring hygiene of a caregiver in a medical treatment venue for example using the system depicted in FIG. 3A, according to some embodiments of the present invention.

For example, FIG. 4 depicts a flowchart of an exemplary method 400 of monitoring hygiene of a caregiver, such as a physician, in a medical treatment venue, such as a clinic, for example using the system depicted in FIG. 3A, according to some embodiments of the present invention. As shown at 401, usage of personal hygiene device(s) in the medical treatment venue is continuously monitored, for example using usage sensors 301, as described above. Then, as shown at 402, a first timing of a personal hygiene event is identified according to the monitoring. As shown at 403, a second timing of a treatment session initiation event during which a new patient is about to participate in a new treatment session at the medical treatment venue is detected, for example using interchange detecting unit 302, as described above. Now, as shown at 404, the first and second timings are matched. This allows, as shown at 405, determining whether to trigger the presentation of an alert and/or to prevent (i.e. withhold) the initiation of the new treatment session, for example using the mechanical barrier and/or controlling software modules that manage patient treatment sessions.

Figure 5A:
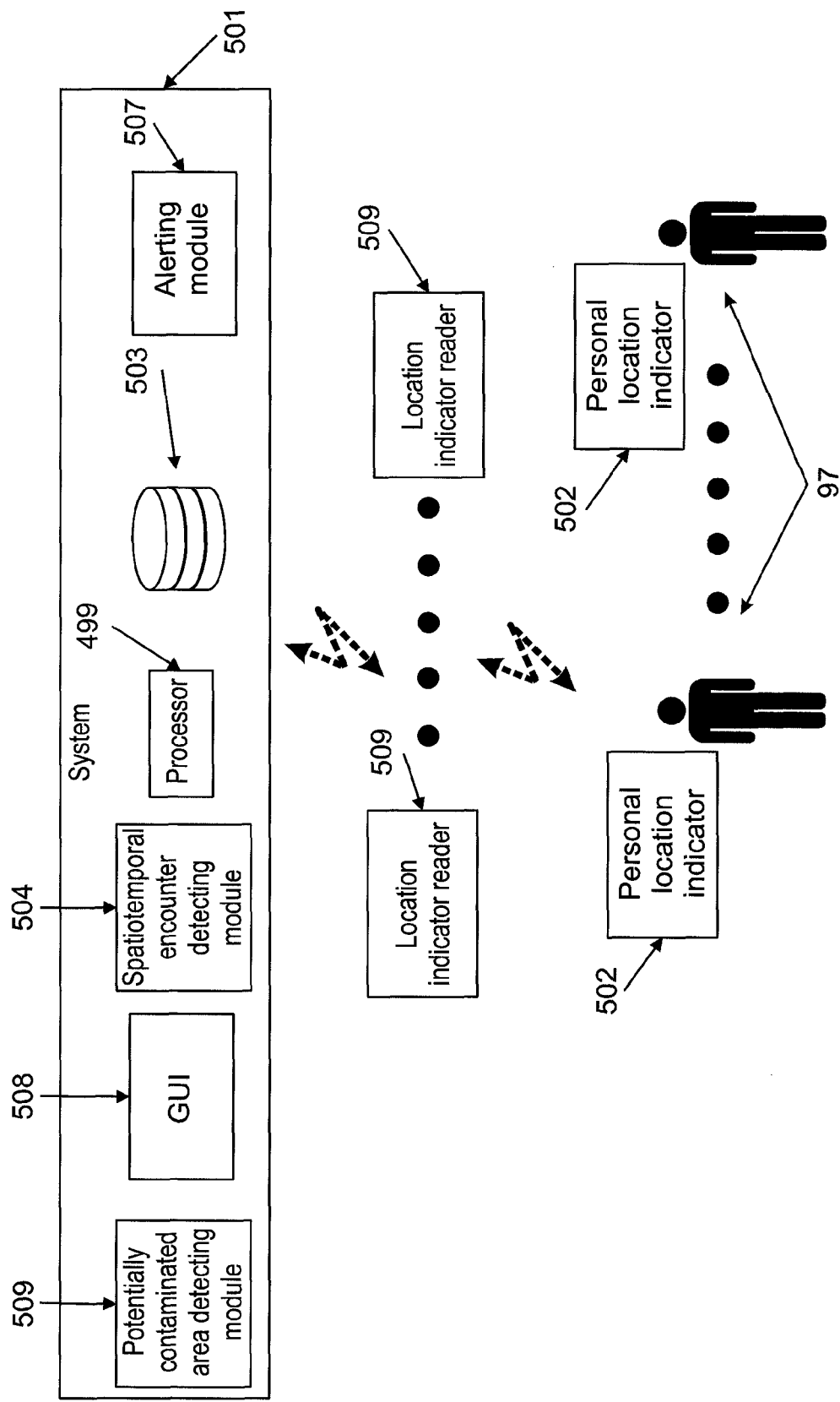
FIG. 5A is a schematic illustration of system of detecting spatiotemporal encounters with one or more infectious persons in a monitored area, according to some embodiments of the present invention.

Reference is now made to FIG. 5A, which is a schematic illustration of system 500 of detecting spatiotemporal encounters with between infectious persons and/or objects and other monitored persons by logging and analyzing movement data of persons in a monitored environment, according to some embodiments of the present invention. The monitored environment may be a hospital, a clinic, a field hospital, a medical center and/or one or more ambulances. The system is based on a central unit 501, for example a processor 499 based computing unit, such as a server, a desktop, a laptop, a tablet, and/or the like and a plurality of personal location indicators 502 which are sized and shaped to be worn and/or carried by persons in the monitored environment, for example hosted in bracelets, name badges, cellular phones, lappet pins and/or the like. Optionally, the personal location indicator 502 includes an indoor location monitoring unit, such as an indoor positioning system (IPS) node in a network of devices used to wirelessly locate objects or people. For example, the personal location indicator 502 is a passive, an active, and/or a semi active radio-frequency identification (RFID) tag. In such an embodiment, a plurality of personal location indicator readers 509 are distributed in the monitored environment to identify a proximity to one or more RFID(s) tags and to report the identification to the central unit 501 for facilitating the mapping of a current location of the persons. Optionally, a dense network of low-range receivers is arranged, for example in a grid pattern, throughout the monitored environment to identify the location of the personal location indicators 502. Optionally, visual coverage with a camera grid is combined with the wireless coverage of the grid pattern. Optionally, the personal location indicator 502 includes an indoor location detector, for example a receiver which receives unique location information from a plurality of beacons spread in the monitored environment. Optionally, the personal location indicator 502 is given to any caregiver and/or visitors that enter the monitored environment. Optionally, a list that associates between the personal location indicators 502 and a plurality of identities is updated continuously.

Optionally, the personal location indicator 502 is implemented as a software module, for example an application, that is installed, either temporarily or permanently in handheld devices of the monitored persons, for example in cellular devices, tablets, and/or the like. For example, the personal location indicator 502 may use the transceiver of the hosting handheld device for identifying and/or signaling its location.

The central unit 501 maps the location information in a database 503. This allows a spatiotemporal encounter detecting module 504 to identify spatiotemporal encounters of one or more infectious persons in the monitored environment. Additionally or alternatively, this allows a potentially contaminated area detecting module 509 to identify areas which potentially infectious persons visited and which may be contaminated so that other person who visited these area may have been also contaminated.

The detection is performed by going over the database 503 to identify persons which met the one or more infectious persons during a specified period and/or been at an infectious location and/or a location which has been visited by one or more infectious persons and the person who visited these locations a certain period thereafter. The spatiotemporal encounter detecting module 504 optionally runes a graphical user interface (GUI) 508 that allows a user to input the identity of one or more infectious persons and to receive a list of persons who encountered the infectious person(s) during a monitored period. Optionally, a spatiotemporal encounter may be defined in different manner. For example, a spatiotemporal encounter may be defined as presence of two or more persons at a certain area for a certain period. The size of the certain area, for example the radius and/or the certain period, for example for how many minutes, may be defined by the user, for example as 5, 10, 15, 20, and 25 minutes.

Figure 6:
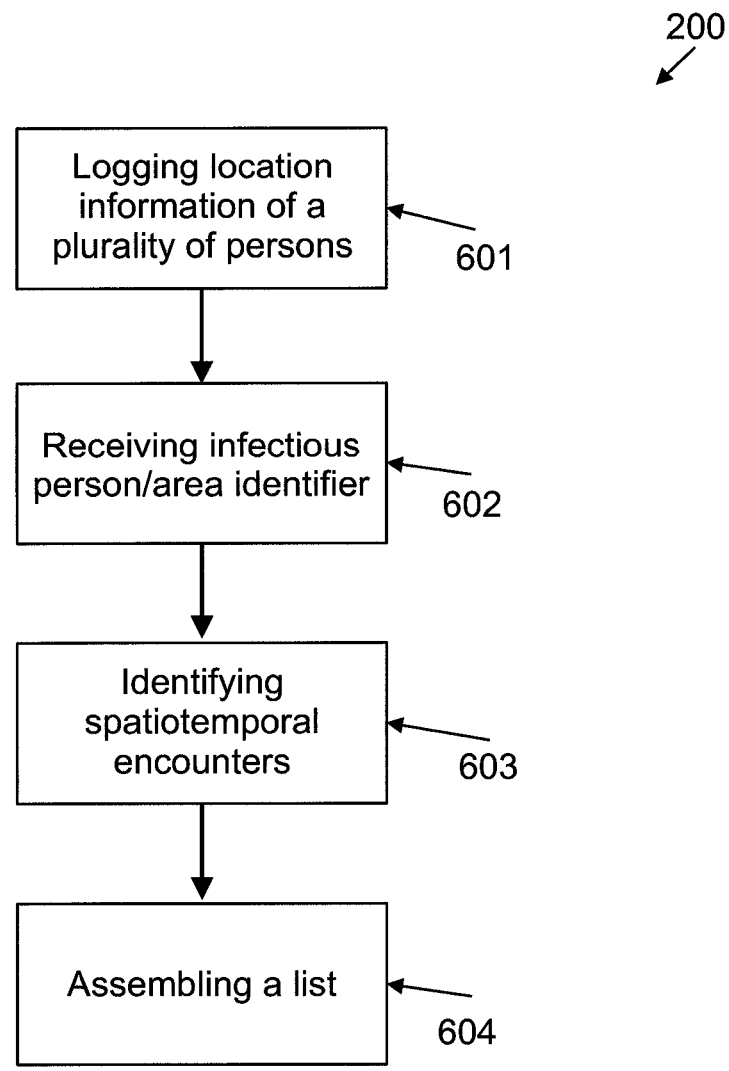
FIG. 6 is a flowchart of a method for detecting spatiotemporal encounters with one or more infectious persons, according to some embodiments of the present invention.

For example, reference is now made to FIG. 6, which is a flowchart 600 of a method for detecting spatiotemporal encounters with one or more infectious persons, according to some embodiments of the present invention.

First, as shown at 601, location information of a plurality of persons in a medical treatment area is logged in a dataset, for example in the database 503 by the central unit 501 using the personal location indicators 502, during a monitoring period of several hours or more, for example 24 hours, several days, weeks, months, and/or years.

Now, as shown at 602, the encounter detecting module 504 receives an identifier of one or more infectious persons from the persons and optionally an estimated infection time and/or an infectious area, for example using the above mentioned GUI 508. Optionally, when an indication of an infectious area is received, one or more potentially infectious persons are identified according to an analysis of the dataset.

As shown at 603, the encounter detecting module 504 now reviews the dataset to identify a plurality of spatiotemporal encounters held after the estimated infection time, between the infectious person(s) and some or all of the persons. The identification may be done using various matching and/or data mining algorithms. This allows the encounter detecting module 504, as shown at 604, to assemble a list of persons from according to the spatiotemporal encounters and to output the list, for example to present it on a display and/or forwarding it to an alerting module. This list may include a first circle of infection, namely all the persons which are monitored and encountered the infectious person after the infection time.

Figure 5B:
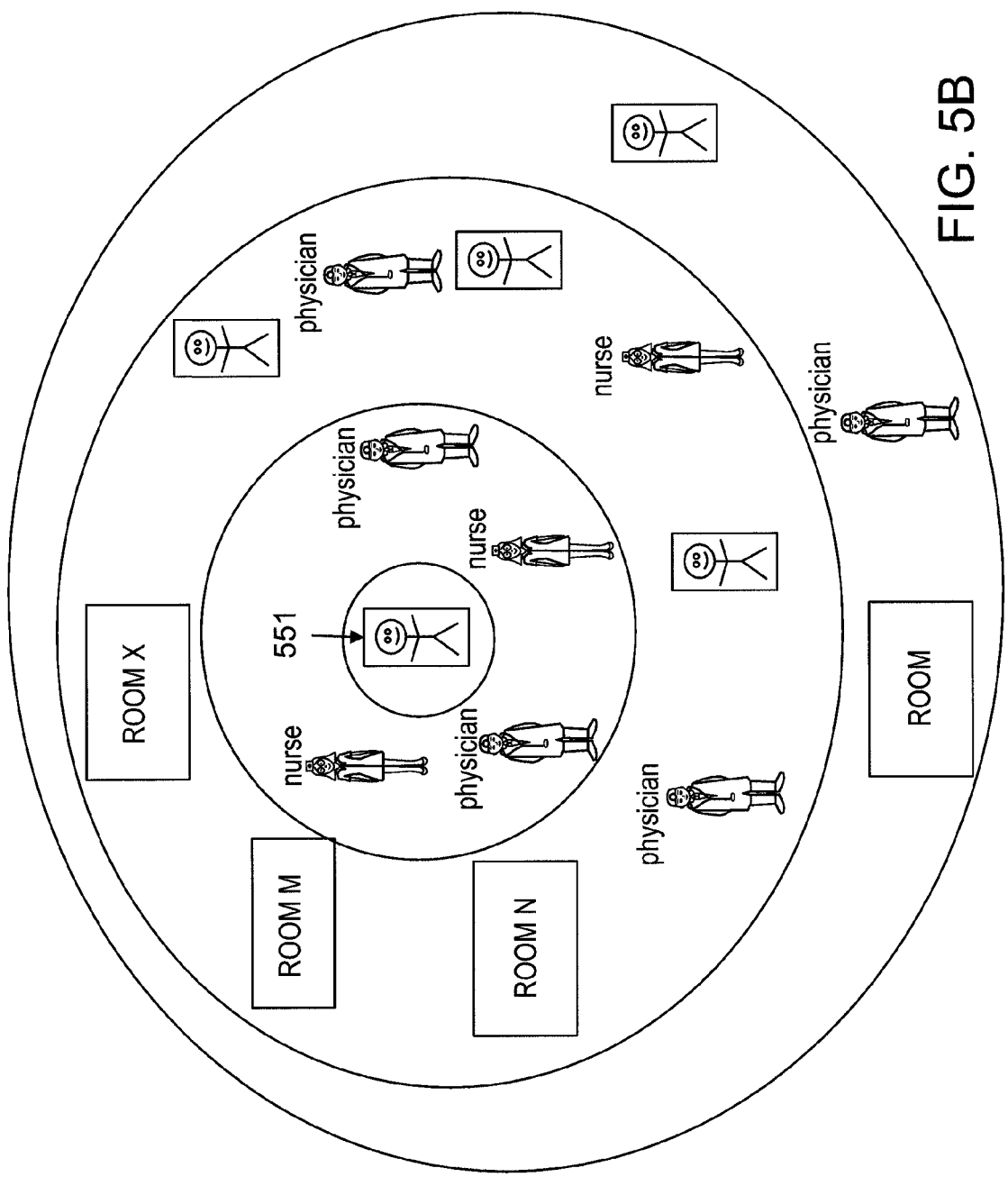
FIG. 5B is a schematic illustration of circles around an infectious area, an exemplary patient bad.

Optionally, encounter detecting module 504 is set to detect spatiotemporal encounters between persons who met the infectious person(s) and other persons by analyzing the dataset, namely identifying a second circle of infection. This process may be repeated for a third circle of infection, fourth circle of infection, and so on and so forth. For example, FIG. 5B depicts circles around an infectious area, an exemplary patient bed 551.

The monitored area may include one or more departments, facilities, buildings, and/or medical centers, facilitating tracking infectious in a spread area. The central unit 501 optionally allows tracking the location of caregivers and patients in real time by querying or otherwise reviewing the dataset. Optionally, each personal location indicator 502 includes a presentation device which communicates with an alerting module 507 of the system 500. This allows sending a notification to be presented to the respective wearer and/or to persons which are located therearound. In such a manner, monitored persons and people therearound may receive a notification about a potential infection in real time. The communication may be based on RF and/or cellular network communication.

Optionally, the encounter detecting module 504 may manage a GUI, such as 508, that may be accessed from remote devices, for example a web service that allows remote access. In such a manner, infection data may be accessed from handheld device and/or other client terminals, such as laptops and/or tablets.

Figure 7:
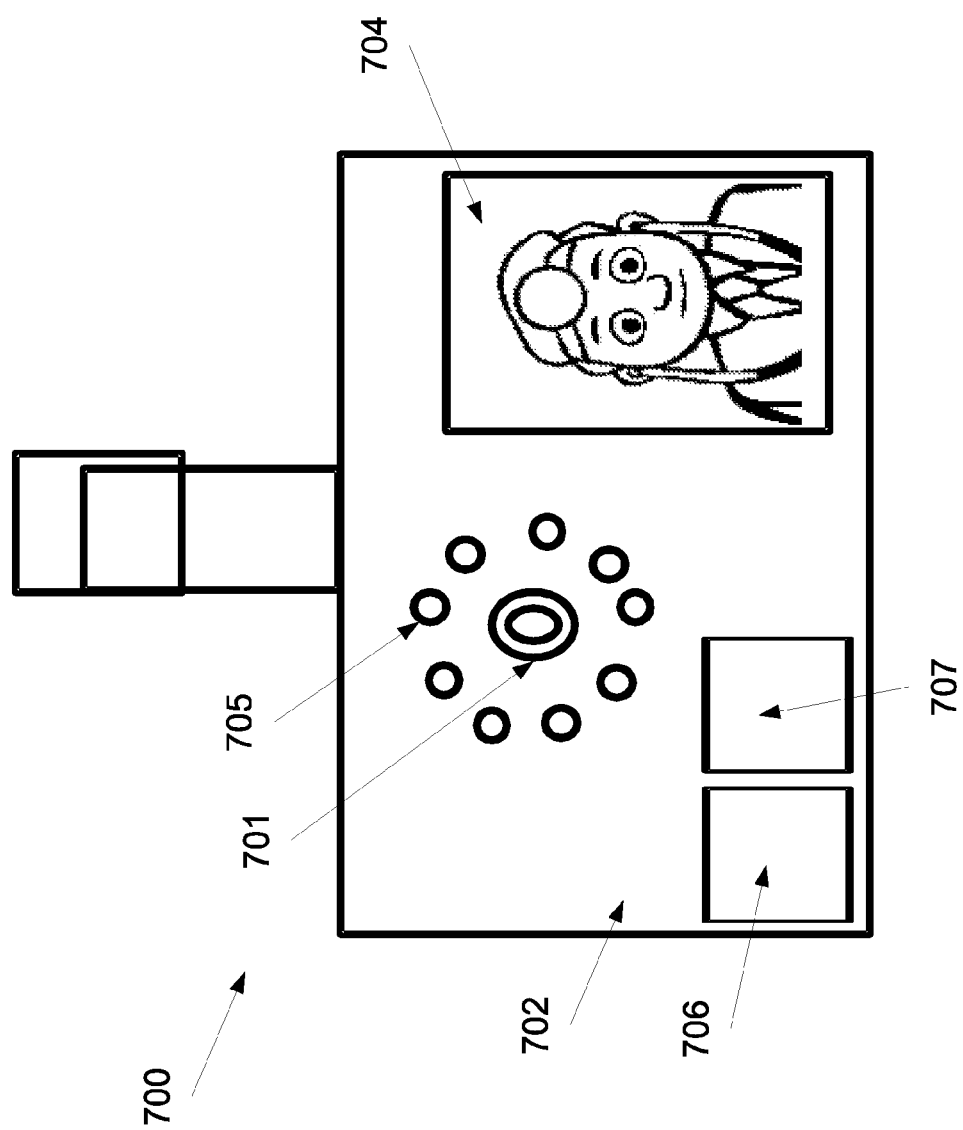
FIG. 7 is a hygiene monitoring name tag that includes a hygiene event sensor for detecting personal hygiene events, such as an image sensor, according to some embodiments of the present invention.
Figure 8D:
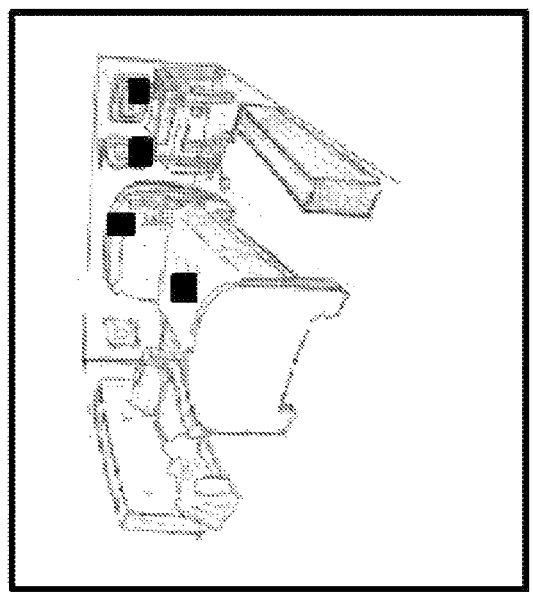
FIGS. 8A-8D are exemplary objects which are tagged to indicate personal hygiene events and potential contamination events, according to some embodiment of the present invention.
Figure 8C:
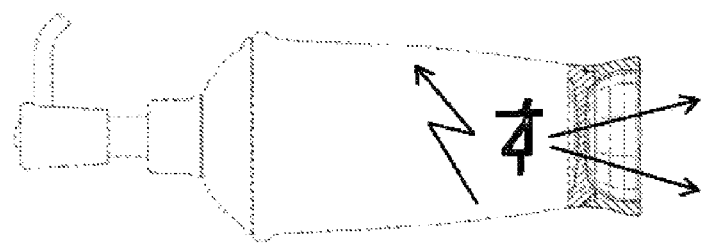

Reference is now made to FIG. 7 which is a hygiene monitoring name tag 700 that includes a hygiene event sensor for detecting personal hygiene events, such as an image sensor 701, according to some embodiments of the present invention, or another hygiene event sensor, for example location sensor and/or beacon that identifies and/or indicates a location. The location sensor may be an IR sensor, an RFID reader, and/or an audio receiver. The location tag may be an IR transmitter, an RFID tag, and/or an RF beacon that emits a signal that encodes a unique ID, for example as shown in FIGS. 8A and 8C. FIG. 8D depicts a various room objects that can be tagged with location tags. When the image sensor 701 is used, the personal hygiene events are detected by analysis of images captured by the image sensor 701. When a location sensor and/or tag is used, the personal hygiene events may be identified according to a match between the detected location and a list indicative of hygiene related location coordinates.

The hygiene monitoring name tag 700 may be used as a tool for monitoring hygiene habits and/or protocols of a wearer, for example as part of a system that monitors hygiene habits and/or protocols of numerous wearers, for example as described in International Patent Application Pub. No. WO2010/026581, which is incorporated herein by reference. Optionally, the monitoring is performed along a period of between few hours and several days, weeks, months, and/or years. Such embodiments allow ranking a plurality of users according to their compliance with hygiene protocols and/or habits in a certain area of interest, such as an institute, a facility, and/or a company, such as a hospital, a factory, a restaurant, a catering service and/or any other institute, facility, and/or company that enforce hygiene habits.

The hygiene monitoring name tag 700 includes an apparatus body 702, for example a plastic injection molded part, shaped and sized as a name tag, for example as shown at FIG. 7. The hygiene monitoring name tag 700 includes an attachment element 703, such as a band and a clamping element, which is set to attach the body to a clothing article worn by a wearer. The apparatus body 702 includes a presentation surface 704, mounted on the apparatus body 702 for displaying an identity of the wearer for others to view, for example a name and/or an image. When an image sensor 701 is used, the hygiene monitoring name tag 700 further includes an image processing module 706 that uses a microprocessor for analyzing images captured by the image sensor 701. Optionally, the apparatus body 702 includes a set of illumination means 705, for example IR, ultraviolet, and/or visible light LEDs for illuminating the surrounding in front of the image sensor 701 The image processing module 706, which is mounted in the apparatus body 702, receives the captured images, for example a video sequence, and identifies, based on image processing analysis, personal hygiene events related to the wearer.

Figure 8B:
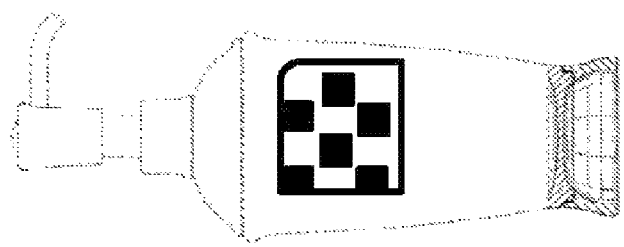
Figure 8A:
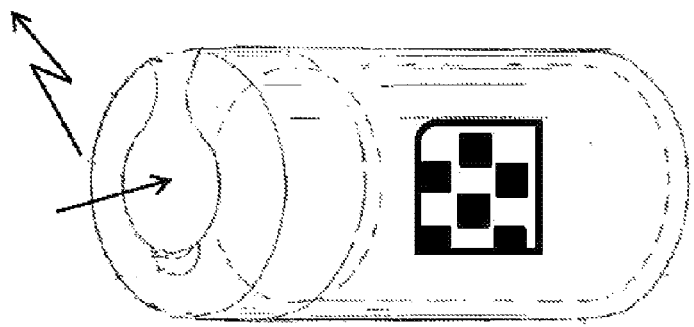

Optionally, the image processing module 706 analyzes image to identify machine-readable labels, such as barcodes, for example QR codes, which are indicative of a hygiene related venues, such as a tap, a moist towelette dispenser, as shown at FIG. 8A, a disinfecting material dispenser, as shown at FIG. 8B, a. Optionally, the image processing module 706 analyzes images to identify a unique signaling sequence. Optionally, the image processing module 706 analyzes images to identify hand washing gestures. This may include measuring quality parameters, for example the period of washing gestures, the washing gestures intensity, the washing gestures type, for example rubbing fingertips and/or the like.

Optionally, the hygiene monitoring name tag 700 further identifies potential contamination venues. The potential contamination venues may be identified according to location, for example a proximity to a patient bed, a presence in an emergency Room, and/or leaving a monitored area and/or by identifying a label indicative of a potential contamination venue, for example identifying a barcode marking a door, a patient bed, and/or the like.

Optionally, a potential contamination venue and/or a hygiene related venue are marked by illumination with a coded frequency and/or coded illumination sequence. The coded information is indicative of the respective location.

Optionally, the hygiene monitoring name tag 700 further identifies potential contamination events, for example a physical checkup of a patient and/or a proximity and/or usage of potential contaminated object, such as a keyboard, a cellular phone, a door knob, a counter desk and/or the like. The identification may be performed by image analysis, for example similarly to the described above.

Optionally, the hygiene monitoring name tag 700 includes a hygiene analysis unit 707 that manages a wearer profile, for example as described above and/or forwards the information about personal hygiene events and/or potential contamination events and/or venues to such a hygiene analysis unit that is managed by a central unit.

The hygiene analysis unit 707 may forward the data to the central unit as described in International Patent Application Pub. No. WO2010/026581, which is incorporated herein by reference. The hygiene analysis unit may locally calculate a current hygiene status by combining personal hygiene events and potential contamination events and/or venues. For example, when a potential contamination event and/or venue is detected, a current hygiene status is set as potentially contaminated as long as no personal hygiene event, optionally in a desired quality, is detected. The current hygiene status may be displayed using a presentation unit on the hygiene monitoring name tag 700. Optionally, if the image sensor is blocked, for example if the captured image is static and/or lack brightness for a certain time and/or an alert is played. Optionally, if the hygiene monitoring name tag 700 is not worn correctly, an alert is played, for example if the captured image is tilted blocked, and/or semi blocked.

According to some embodiment of the present invention, a personal hygiene monitor as defined in International Patent Application Pub. No. WO2010/026581, which is incorporated herein by reference is used. For example, the components of the personal hygiene monitor are incorporated in an armlet, a wristwatch, a ring, a necklace, a band or any wearable device that is designed to be attached to the user while she performs duties which require relatively high level of hygiene.

In some embodiments of the present invention, the personal hygiene monitor includes a processor, such as a microcontroller, which is connected to a memory unit, such as a flash memory and one or more hygiene event sensors. The one or more hygiene event sensors are designed to detect, separately and/or in combination, a personal hygiene event. For example, a personal hygiene event may be detected if only one of the hygiene event sensors detects a personal hygiene event above a predefined value, for example as further described below, or if a sum, a mean, and/or an average value of the readings made by the hygiene event sensors are above a predefined threshold. Each one of the hygiene event sensors is designed for detecting a personal hygiene event according to a physical stimulus and/or a set of physical stimulations, such as thermal energy, electromagnetic energy, acoustic energy, pressure, magnetism, and/or motion and producing a signal, usually electrical for indicating this detection and/or optionally the quality of this detection, for example as described in International Patent Application Pub. No. WO2010/026581.

Optionally, the personal hygiene monitor matches temporal information or spatiotemporal information about personal hygiene events with temporal information or spatiotemporal information about patient treatments, for example from an EMR system.

Figure 9:
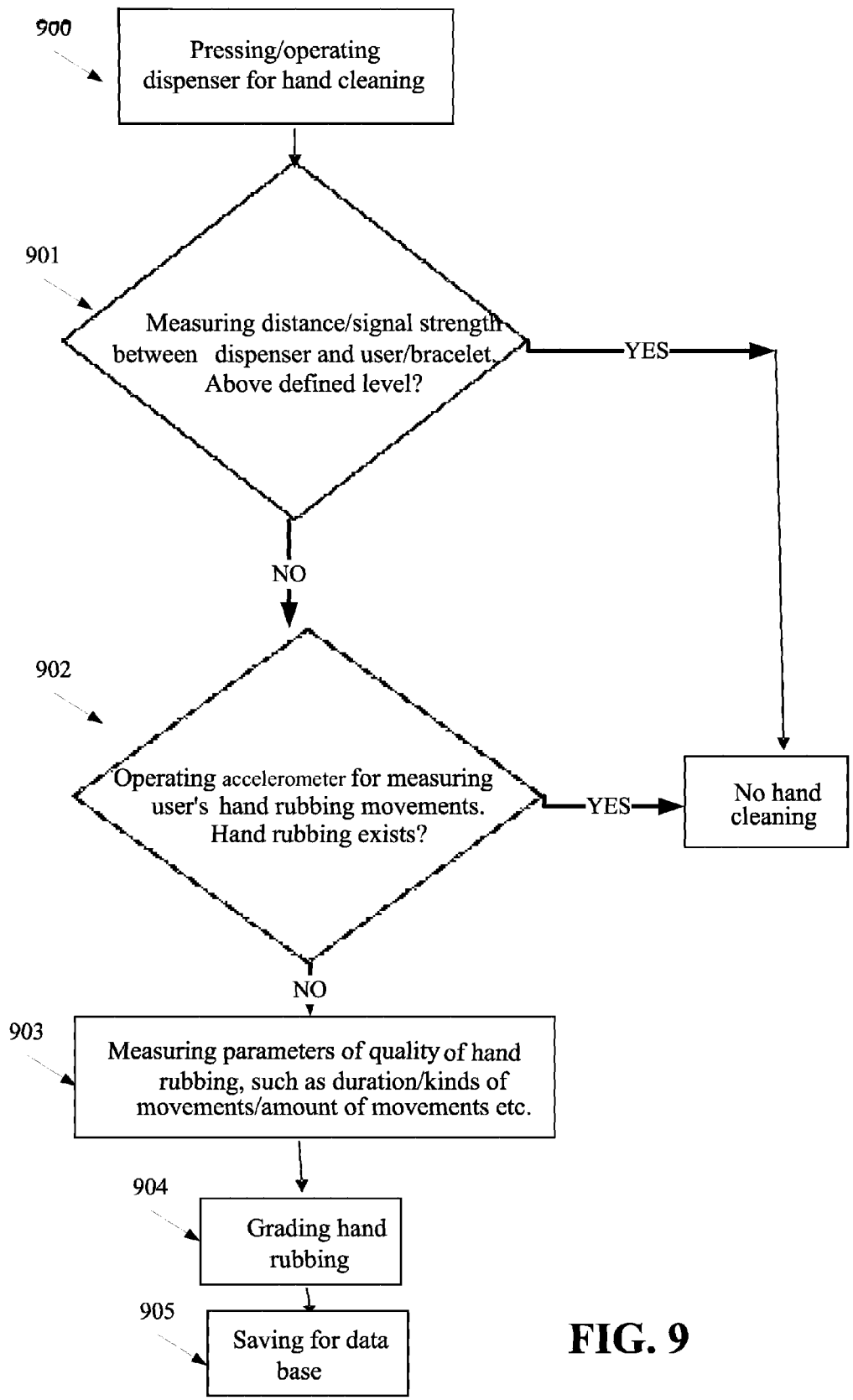
FIG. 9 is a flowchart of an exemplary process of detecting personal hygiene motion pattern indicative of hand washing, according to some embodiment of the present invention.

Optionally, the personal hygiene monitor includes a motion detection sensor, such as an accelerometer and a gyroscope, which monitors the motion of the personal hygiene monitor to detect personal hygiene motion patterns. Such a monitoring allows tracking gestures of the user and comparing them with one or more movement patterns each defines gestures taken during a respective personal hygiene event, such as washing hands or replacing a robe and/or a pair of gloves. Optionally, the personal hygiene monitor identifies a hand washing event by detecting a sequence of events, for example pressing a dispenser button, measuring signal strength, and identifying a hand washing movement. Optionally, time of sub actions is measured. See, for example, FIG. 9 which is a flowchart of an exemplary process of detecting personal hygiene motion pattern indicative of hand washing, according to some embodiment of the present invention. The process may be initiated when a dispenser is operated, for example by a pressure sensor that is connected to a controller, as shown at 900. In this method, as shown at 901, a distance between a hand worn personal hygiene monitoring device having an accelerometer and a proximity sensor located in proximity to a hand hygiene device such as a tap, a liquid dispenser, a powder dispenser, a soap stand and a towelette dispenser is measured. Then, as shown at 902, when the distance is below a certain value, a movement of said hand worn personal hygiene monitoring device in proximity to the proximity sensor is detected. As shown at 903, one or more characteristics of the movement are evaluated by analyzing an output of the accelerometer, for example speed, movement pattern, repetitions and/or the like. This allows measuring the quality of the movement and optionally scoring and/or grading the movement, as shown at 904. The score may be stored, as shown at 905 and used for user hygiene scoring, for example as shown at International Application No. PCT/EP2006/062895, filed on Jun. 2, 2006 and/or outputted.

In some embodiments of the present invention, the personal hygiene monitor is integrated and/or includes a personal disinfecting material dispenser that is carried by a monitored user and set to identify when disinfecting materials are used.

It is expected that during the life of a patent maturing from this application many relevant methods and systems will be developed and the scope of the term a module, a processor, a network, a beacon, and a node is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of monitoring neonatal incubator hygiene, the method comprising:
   continuously monitoring a current hygiene level of a plurality of caregivers by detecting, per each one of said caregivers, a plurality of personal hygiene events held during a monitoring period;
   identifying a care giving event every time one of said plurality of caregivers is proximate to one of a plurality of neonatal incubators; and
   generating an alert based on:
   (a) said current hygiene level when said care giving event is identified;

(b) for a certain one of the caregivers, no detection of a personal hygiene event between two identifications of care giving events of two different ones of the neonatal incubators.

2. The method of claim 1, wherein said identifying comprises receiving a signal indicative of a proximity to said one of the plurality of neonatal incubators from a beacon associated with said one of said plurality of neonatal incubators.

3. The method of claim 1, wherein said hygiene level is estimated according to a wearable sensor worn by said one of said plurality of caregivers.

4. The method of claim 1, wherein said care giving event is identified when the hands of said one of said plurality of caregivers are detected in a chamber of said one of said plurality of neonatal incubators.

5. A system for monitoring neonatal incubator hygiene in a ward, the system comprising:
 a plurality of hygiene monitors configured to monitor continuously a current hygiene level of a plurality of caregivers by detecting a plurality of personal hygiene events related to said plurality of caregivers;
 a plurality of neonatal incubator sensors each configured to identify a care giving event every time one of said plurality of caregivers is proximate to one of a plurality of neonatal incubators; and
 a central unit configured to receive data from said plurality of hygiene monitors and said plurality of neonatal incubator sensors, to generate an alert if said current hygiene level is below a threshold when a respective said care giving event is identified, and if, for a certain one of the caregivers, no personal hygiene event is identified between two identifications of care giving events of two different ones of the neonatal incubators.

6. The system of claim 5, wherein each said neonatal incubator sensor is configured to detect an insertion of a hand into a chamber of a respective said neonatal incubator as said care giving event.

7. The system of claim 5, wherein each said hygiene monitor comprises an image sensor, and wherein said central unit is configured to detect said personal hygiene event by an analysis of a plurality of images captured by said image sensor.

8. The system of claim 5, wherein at least some of said plurality of hygiene monitors are stationary and disposed to image at least a portion of a medical treatment area in which said plurality of neonatal incubators are located.

9. A system for monitoring neonatal incubator hygiene in a neonatal incubator, comprising:
 a usage monitor configured to detect usage in a personal hygiene device by a caregiver;
 a neonatal incubator sensor configured to identify a care giving event during which a caregiver is proximate to a neonatal incubator; and
 a controller configured to receive data from said usage monitor and said neonatal incubator sensor to generate an alert according to:
  (a) a match between said usage and said care giving event, and
  (b) a determination that no usage of the personal hygiene device by the caregiver is detected before identification of care giving event of the neonatal incubator and after another care giving event of another neonatal incubator.

10. The system of claim 9, wherein each said neonatal incubator sensor is further configured to detect an insertion of a hand into a chamber of a respective said neonatal incubator as said care giving event.

11. The system of claim 9, further comprising a hygiene monitor which comprises an image sensor, and wherein said controller is configured to detect said personal hygiene event by an analysis of a plurality of images captured by said image sensor.

12. The system of claim 11, wherein said hygiene monitor is stationary and disposed to image at least a portion of a medical treatment area in which said neonatal incubator is located.

* * * * *